(12) United States Patent
Strand et al.

(10) Patent No.: US 10,441,523 B2
(45) Date of Patent: *Oct. 15, 2019

(54) REGIMEN FOR CONTROLLING OR REDUCING DENTINE HYPERSENSITIVITY

(71) Applicant: The Procter & Gamble Company, Cincinnati, OH (US)

(72) Inventors: Ross Strand, Singapore (SG); Alastair Robert Edward MacGregor, Englefield Green (GB); Claire Goodall, Surbiton (GB)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/161,160

(22) Filed: May 20, 2016

(65) Prior Publication Data

US 2016/0263007 A1 Sep. 15, 2016

(51) Int. Cl.
| | | |
|---|---|---|
| A61K 8/24 | (2006.01) |
| A61Q 11/00 | (2006.01) |
| A61K 33/06 | (2006.01) |
| A61K 8/55 | (2006.01) |
| A61K 31/6615 | (2006.01) |
| A61K 33/42 | (2006.01) |
| A61K 8/21 | (2006.01) |

(52) U.S. Cl.
CPC ............... *A61K 8/556* (2013.01); *A61K 8/21* (2013.01); *A61K 8/24* (2013.01); *A61K 8/55* (2013.01); *A61K 31/6615* (2013.01); *A61K 33/42* (2013.01); *A61Q 11/00* (2013.01); *A61K 2800/884* (2013.01); *A61K 2800/92* (2013.01)

(58) Field of Classification Search
CPC .... A61C 19/066; A46B 15/0091; A61K 8/21; A61K 8/22; A61K 2800/884; A61Q 11/00
USPC ........................................................ 424/49
See application file for complete search history.

(56) References Cited

U.S. PATENT DOCUMENTS

| | | |
|---|---|---|
| 2,955,984 A | 10/1960 | Gabriel |
| 4,183,915 A * | 1/1980 | Gaffar ............... A61K 8/21 424/49 |
| 4,988,499 A | 1/1991 | Bristow et al. |
| 5,460,803 A | 10/1995 | Tung |
| 5,562,895 A | 10/1996 | Tung |
| 5,833,954 A | 11/1998 | Chow |
| 5,993,786 A | 11/1999 | Chow |
| 6,592,852 B1 | 7/2003 | Ryles |
| 2003/0202945 A1 | 10/2003 | Ryles |
| 2003/0231698 A1 | 12/2003 | Yamaguchi et al. |
| 2006/0171904 A1 | 8/2006 | Vogel et al. |
| 2006/0292090 A1 | 12/2006 | Sharma |
| 2006/0292092 A1 | 12/2006 | Sharma |
| 2007/0207092 A1 | 9/2007 | Riina |
| 2008/0247973 A1 | 10/2008 | Baig |
| 2009/0269287 A1 | 10/2009 | Berta |
| 2010/0129298 A1 | 5/2010 | Sakuma et al. |
| 2010/0203092 A1 | 8/2010 | Ley et al. |
| 2011/0089073 A1 | 4/2011 | Baig |
| 2011/0243861 A1 * | 10/2011 | Vierling ............... A61K 8/044 424/58 |
| 2017/0333326 A1 | 11/2017 | Strand |

FOREIGN PATENT DOCUMENTS

| | | |
|---|---|---|
| CN | 1751678 | 3/2006 |
| EP | 1061892 | 12/2000 |
| EP | 952851 | 5/2011 |
| EP | 2143415 | 7/2015 |
| JP | 10109915 | 4/1998 |
| JP | 2000044447 | 2/2000 |
| JP | 3971877 | 9/2007 |
| WO | WO9620693 | 7/1996 |
| WO | WO9947108 | 9/1999 |
| WO | WO2007002887 | 1/2007 |
| WO | WO200805509 | 1/2008 |

OTHER PUBLICATIONS

AA899C International Search Report with written opinion, dated Apr. 4, 2015, 10 pages.
All Office Actions, U.S. Appl. No. 15/790,877.
Tung Ming S et al: "Amorphous calcium phosphates for tooth mineralization.", Compendium of Continuing Education in Dentistry (Jamesburg, N.J. : 1995) Sep. 2004, vol. 25, No. 9 Suppl1, Sep. 2004; (Sep. 2004), pp. 9-13.

* cited by examiner

*Primary Examiner* — Lezah Roberts
(74) *Attorney, Agent, or Firm* — James E. Oehlenschlager; Jason J Camp (57) ABSTRACT

The present invention provides a method of treating a tooth surface to control or reduce dentine hypersensitivity, comprising the steps: (a) contacting the tooth surface with a first composition comprising an organophosphate; and thereafter (b) contacting the tooth surface with a second composition comprising a water-insoluble calcium phosphate.

18 Claims, 6 Drawing Sheets

| | (a) Water | (b) A6 then B2 | (c) B2 then A6 |
|---|---|---|---|
| Open Dentine Tubules (Before Treatment) |  |  |  |
| Brush 1 min with Oral B® Pro-Expert toothpaste |  |  |  |
| Immerse 3 min in Water or Rinse (after 5 cyclesthe) |  |  |  |
| Immerse 5min in Coca-Cola |  |  |  |
| Immerse 2min in 1% citric acid |  |  |  |

REGIMEN FOR CONTROLLING OR REDUCING DENTINE HYPERSENSITIVITY

FIELD OF THE INVENTION

The present invention relates to a method of treating tooth surface with a first composition and then a second composition to control or reduce dentine hypersensitivity.

BACKGROUND OF THE INVENTION

Tooth surfaces are constantly experiencing a loss and gain of minerals. This process is partially kept in balance by the chemical composition of saliva and extra-cellular fluid. Disruption of the tooth surface integrity can occur by acidic food and beverages, bacterial challenge and erosion by exaggerated tooth brushing or grinding of the teeth. These processes are accompanied by a demineralization of the exposed tooth surfaces leading to clinical conditions such as dentine hypersensitivity.

Dentine hypersensitivity, also called tooth sensitivity, is a temporary induced pain sensation produced when hypersensitive teeth are subjected to changes in temperature and/or pressure or to chemical action. Hypersensitivity may occur when the dentin of a tooth is exposed due to, for example, demineralization. Dentine generally contains channels, called tubules, that allow material and energy transport between the exterior of the dentin and the interior of the tooth where the nerve is located. Exposure of these tubules to external stimuli can cause irritation of the nerve and lead to the discomfort or pain of hypersensitivity.

Many attempts have been made to control dentine hypersensitivity. One approach is to reduce the excitability of the nerve in a sensitive tooth by altering the chemical environment of the nerve to make the nerve less sensitive. Some "nerve agents" or "nerve desensitizing agents", such as potassium nitrate, are generally used for this purpose. Another approach is to fully or partially block or occlude the tubules so as to prevent or limit exposure of the nerve to external stimuli. The agents for this purpose are referred to as "tubule blocking agents". Charged polystyrene beads, polyacrylic acid, apatite, and some polyelectrolytes have been reported as tubule blocking agents.

Despite these attempts, there continues to be a need for effectively controlling dentine hypersensitivity. There continues to be a need for reducing dentine hypersensitivity. There continues to be a need for preventing dentine hypersensitivity. There continues to be a need for a long-lasting efficacy in controlling dentine hypersensitivity.

SUMMARY OF THE INVENTION

The present invention attempts to solve one or more of these problems. In one aspect, the present invention provides a method of treating a tooth surface, comprising the steps:

(a) contacting the tooth surface with a first composition comprising an organophosphate having the formula:

wherein R is a hydrocarbyl comprising 4 to 22 carbon atoms; X and Y are each independently an alkylene comprising 2 to 4 carbon atoms; a and b are each independently an integer selected from 0 to 20, and wherein a+b is in the range from 0 to 20; $Z^1$ and $Z^2$ are each independently selected from hydrogen, hydrocarbyl comprising 1 to 26 carbons preferably comprising one or more ether moieties, and a counter ion, provided that at least one of $Z^1$ and $Z^2$ is hydrogen or a counter ion; and thereafter (b) contacting the tooth surface with a second composition comprising a water-insoluble calcium phosphate, wherein the water-insoluble calcium phosphate has a calcium to phosphorus molar ratio from 1:1 to 10:1.

In another aspect, the present invention provides an oral care kit, comprising:

(a) a first product containing a first composition, wherein the first composition comprises 0.01% to 99%, by weight, of an organophosphate as defined above;

(b) a second product containing a second composition, wherein the second product is a mouth rinse with a pH from 7 to 10 and a viscosity from 2000 cps to 8000 cps, and wherein the second composition comprises 0.01% to 99%, by weight, of a water-insoluble calcium phosphate having a calcium to phosphorus molar ratio from 1:1 to 10:1; and (c) instructions instructing a user to first use the first product to contact a tooth surface and thereafter immediately use the second product to contact the tooth surface.

In a further aspect, the present invention provides an oral care product comprising a first container and a second container, wherein the first container contains a first composition comprising 0.01% to 99%, by weight, of an organophosphate as defined above; wherein the second container contains a second composition comprising 0.01% to 99%, by weight, of a water-insoluble calcium phosphate which has a calcium to phosphorus molar ratio from 1:1 to 10:1; and wherein the product optionally contains instructions instructing a user to dispense the first composition before the second composition is dispensed.

One aspect of the invention generally provides a sequential application system of a specific organophosphate followed by a water-insoluble calcium phosphate onto tooth surface. Without wishing to be bound by theory, the first step of applying the specific organophosphate is believed to treat and modify the tooth surface to be hydrophobic. The organophosphate has affinity to apatite on the tooth surface and therefore can deposit and adhere to the tooth surface forming a hydrophobic coating having prolonged retention thereon. The second step of applying the water-insoluble calcium phosphate is believed to block or occlude the tubules exposed on the tooth surface. In other words, the exposed tubules, along with the hydrophobic coating, constitute traps for capturing the calcium phosphate, and the calcium phosphate, in turn, seals the tubules so as to prevent or limit exposure of the nerve inside the tubules to external stimuli. By this sequential application system, perceptible and meaningful improvements are delivered to the tooth surface, by potentially providing new crystal growth at sites of enamel loss or thinning, blocking or occluding the exposed tubules and building up a protection layer to prolong the tubule occlusion.

These and other features, aspects, and advantages of the present invention will become evident to those skilled in the art from the detailed description which follows.

BRIEF DESCRIPTION OF THE DRAWINGS

While the specification concludes with claims particularly defining and distinctly claiming the invention, it is believed that the invention will be better understood from the following description of the accompanying figures. In the accompanying figures.

DETAILED DESCRIPTION OF THE INVENTION

The terms "oral composition" and "oral care composition" are used interchangeably herein, and refer to a product, which in the ordinary course of usage, is not intentionally swallowed for purposes of systemic administration of particular therapeutic agents, but is rather retained in the oral cavity for a time sufficient to contact dental surfaces and/or oral tissues for purposes of topical administration.

The term "dentifrice", as used herein, includes paste, gel, liquid, powder or tablet formulations for cleaning teeth with the aid of a toothbrush unless otherwise specified. The dentifrice composition may be a single phase composition or may be a combination of two or more separate dentifrice compositions.

The term "water-insoluble", as used herein, means having a low solubility in water or being incapable of being fully dissolved in water. Specifically, a water-insoluble substance is intended to mean a substance which has a solubility at 20° C. of less than 1 g/l and in particular of less than 1 mg/l.

The term "water-soluble", as used herein, means having a high solubility in water or being capable of being fully dissolved in water. Specifically, a water-soluble substance is intended to mean a substance which has a solubility at 20° C. of no less than 1 g/l and in particular of no less than 10 g/l.

The term "particle size", as used herein, refers to a volume based particle size measured by laser diffraction methods. Laser diffraction measures particle size distributions by measuring the angular variation in intensity of light scattered as a laser beam passes through a dispersed particulate sample. Large particles scatter light at small angles relative to the laser beam and small particles scatter light at large angles. The angular scattering intensity data is then analyzed to calculate the size of the particles responsible for creating the scattering pattern, using the Mie theory of light scattering. The particle size is reported as a volume equivalent sphere diameter. The term "mean particle size" and "average particle size" are used interchangeably herein, and refer to an average value of particle size distribution calculated based on the logarithmic scale.

The terms "hydrocarbyl", "hydrocarbyl substituent" and "hydrocarbyl group" are used interchangeably herein, and refer to a univalent radical having a carbon atom directly attached to the remainder of the molecule and having predominantly hydrocarbon character. Such a univalent radical can be classified as an aliphatic group, cyclic group, or combination of aliphatic and cyclic groups (e.g., alkaryl and aralkyl groups). The term "aliphatic group" means a saturated or unsaturated linear or branched hydrocarbon group. This term is used to encompass alkyl, alkenyl, and alkynyl groups, for example. The term "alkyl group" means a saturated linear or branched hydrocarbon group including, for example, methyl, ethyl, isopropyl, t-butyl, heptyl, dodecyl, octadecyl, amyl, 2-ethylhexyl, and the like. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polynuclear aromatic hydrocarbon group.

The term "viscosity", as mentioned herein, is measured using Brookfield viscometers with cone and plate attachment. For viscosities in the range of 0-16000 cps, the Brookfield DV-II viscometer with S02 plate is used. A 500 ml sample of the composition is equilibrated at 25° C. for three minutes before the readings are taken at 2.5 rpm. For viscosities greater than 16000 cps and up to 33000 cps, the Brookfield DV-I viscometer with S02 plate is used. A 500 ml sample of the composition is equilibrated for 1 minute at 25° C. before the readings are taken at 0.3 rpm.

The term "tooth" or its plural form "teeth", as used herein, refers to natural tooth as well as artificial tooth or dental prosthesis.

Active and other ingredients useful herein may be categorized or described by their cosmetic and/or therapeutic benefit or their postulated mode of action or function. However, it is to be understood that the active and other ingredients useful herein can, in some instances, provide more than one cosmetic and/or therapeutic benefit or function or operate via more than one mode of action. Therefore, classifications herein are made for the sake of convenience and are not intended to limit an ingredient to the particularly stated application or applications listed.

As used herein, the articles including "a" and "an" when used in a claim, are understood to mean one or more of what is claimed or described.

As used herein, the terms "comprise", "comprises", "comprising", "include", "includes", "including", "contain", "contains", and "containing" are meant to be non-limiting, i.e., other steps and other sections which do not affect the end of result can be added. The above terms encompass the terms "consisting of" and "consisting essentially of".

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

Sequential Application System

In accordance with the present invention, a sequential application system is provided to treat the tooth surface.

In the first step (a), the tooth surface is contacted with a first composition comprising the organophosphate as defined hereinabove. The organophosphate can deposit and adhere to the tooth surface and form a hydrophobic coating on the tooth surface.

In the second step (b), the tooth surface is further contacted with a second composition comprising a water-insoluble calcium phosphate, wherein the water-insoluble calcium phosphate has a calcium to phosphorus molar ratio from 1:1 to 10:1. The water-insoluble calcium phosphate particles can be trapped by the exposed tubules and therefore deposit into and seal the tubules so as to prevent or limit exposure of the nerve inside the tubules to external stimuli.

In a specific embodiment, contacting step (b) is initiated within 30 minutes, within 15 minutes, within 5 minutes, or immediately after the conclusion of contacting step (a). It is preferred that there is no intervening dental treatment step between step (a) and step (b).

The contacting steps can be achieved by any oral care hygiene regimen, for example, selected from the group consisting of brushing, flossing, rinsing, plastering, attaching, and combinations thereof. Accordingly, the first composition and the second composition can be in various forms to facilitate the oral care hygiene regimen. Such forms include but are not limited to toothpaste, tooth powder, tooth gel, dental floss, mouth rinse, chewable tablet, chewing gum, or strip or film for direct application or attachment to the tooth surface. In a specific embodiment, the first composition is a toothpaste composition and the second composition is a mouth rinse. In another specific embodiment, the first composition and the second composition are each independently a mouth rinse.

The contacting duration depends on the specific regimen and the specific composition form. For example, brushing with a toothpaste may be conducted from 1 to 5 minutes, rinsing with a mouth rinse may be conducted from 5 seconds to 2 minutes, plastering with a strip or film may be conducted from 5 minutes to 60 minutes, preferably from 20 minutes to 40 minutes.

In a specific embodiment, contacting steps (a) and (b) each independently has a contacting duration from 5 seconds to 5 minutes; and contacting step (b) is initiated immediately after the conclusion of contacting step (a).

In a specific embodiment, contacting step (a) is achieved by brushing the tooth surface with a toothpaste comprising the first composition, and then contacting step (b) is immediately achieved by rinsing the tooth surface with a mouth rinse comprising the second composition.

In another specific embodiment, contacting step (a) is achieved by rinsing the tooth surface with a first mouth rinse comprising the first composition, and then contacting step (b) is immediately achieved by rinsing the tooth surface with a second mouth rinse comprising the second composition.

The First Composition

According to the present invention, the first composition comprises a specific organophosphate compound. The organophosphate compound has a strong affinity for enamel surfaces, like teeth, and has a sufficient surface binding propensity to desorb pellicle proteins and remain affixed to enamel surfaces. Without wishing to be bound by any theory, it is believed that, when applied according to the present invention, the organophosphate compound adheres to the teeth, with the phosphate groups binding the calcium in teeth and thus preventing loss of calcium from dissolution into acidic saliva. The organophosphate may also deposit a protective surface coating that is hydrophobic and prevents teeth from coming into direct contact with erosive acids or other harmful substances.

In particular, the first composition comprises an organophosphate having the formula:

wherein R is a hydrocarbyl comprising 4 to 22 carbon atoms; X and Y are each independently an alkylene comprising 2 to 4 carbon atoms; a and b are each independently an integer selected from 0 to 20, and a+b is in the range from 0 to 20; $Z^1$ and $Z^2$ are each independently selected from hydrogen, hydrocarbyl comprising 1 to 26 carbons preferably comprising one or more ether moieties, and a counter ion, provided that at least one of $Z^1$ and $Z^2$ is hydrogen or a counter ion.

Examples of hydrocarbyl groups useful herein include, but are not limited to: (1) hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form an alicyclic radical) and equivalents thereof; (2) substituted hydrocarbon substituents, that is, substituents containing non-hydrocarbon groups which, in the context of the description herein, do not alter the predominantly hydrocarbon substituent (e.g., halo (especially chloro and fluoro), hydroxy, alkoxy, mercapto, alkylmercapto, nitro, nitroso, and sulfoxy) and equivalents thereof; (3) hetero-substituents, that is, substituents which, while having a predominantly hydrocarbon character, in the context of this description, contain other than carbon in a ring or chain otherwise composed of carbon atoms and equivalents thereof. Heteroatoms include sulfur, oxygen, nitrogen, and encompass substituents such as pyridyl, furyl, thienyl and imidazolyl. In a specific embodiment, no more than two, preferably no more than one, non-hydrocarbon substituent is present for every ten carbon atoms in the hydrocarbyl group. In a further specific embodiment, there is no non-hydrocarbon substituent in the hydrocarbyl group.

The presence of the hydrocarbyl group is believed to impart to the compound a degree of hydrophobicity, so that the organophosphate can effectively form a hydrophobic layer on the tooth surface. Such a hydrophobic layer can protect the enamel from erosive acidic challenges and stain deposition.

Some examples of the organophosphate include, but are not limited to, alkyl phosphates and alkyl (poly)alkoxy phosphates, such as lauryl phosphate (tradenames MAP 230K and MAP 230T commercially available from Croda, Snaith, UK); PPGS ceteareth-10 phosphate (Crodaphos SG commercially available from Croda, Snaith, UK); laureth-1 phosphate (tradenames MAP L210 commercially available from Rhodia, La Defense, France, Phosten HLP-1 commercially available from Nikkol Chemical, Tokyo, Japan, or Sunmaep L commercially available from Sunjin Chemical, Korea); laureth-3 phosphate (tradenames MAP L130 commercially available from Rhodia, La Defense, France, Foamphos L-3 commercially available from Alzo, NJ, U.S., or Emphiphos DF 1326 commercially available from Huntsman Chemical, Texas, U.S.); laureth-9 phosphate (tradename Foamphos L-9 commercially available from Alzo, NJ, U.S.); trilaureth-4 phosphate (tradenames Hostaphat KL 340D commercially available from Clariant, Muttenz, Switzerland, or TLP-4 commercially available from Nikkol Chemical, Tokyo, Japan); C12-18 PEG 9 phosphate (tradename Crafol AP261 commercially available from Cognis, Ludwigshafen, Germany); sodium dilaureth-10 phosphate (tradename DLP-10 commercially available from Nikkol Chemical, Tokyo, Japan).

Particularly preferred organophosphates are those containing alkoxy groups, especially repeating alkoxy groups, $(O-X)_a(O-Y)_b$, in particular those containing 1 or more ethoxy, propoxy, isopropoxy, butoxy groups or combinations thereof. The presence of the alkoxy group is believed to increase the solubility of the compound and balance the amphiphilicity of the compound, so that the hydrophilic phosphate head can "stick" to the tooth surface (given its charge) while the hydrophobic hydrocarbyl tail is extended to a long carbon chain. On the other hand, the presence of the alkoxy group can help diffusing substances away from the tooth surface.

Additional suitable organophosphates may include alkyl mono glyceride phosphate, alkyl sorbitan phosphate, alkyl methyl glucoside phosphate, alkyl sucrose phosphates, dextran phosphate, polyglucoside phosphate, alkyl polyglucoside phosphate, polyglyceryl phosphate, alkyl polyglyceryl phosphate, polyether phosphates and alkoxylated polyol phosphates. Some specific examples may include polyethylene glycol (PEG) phosphate, polypropylene glycol (PPG) phosphate, alkyl PPG phosphate, PEG/PPG phosphate, alkyl PEG/PPG phosphate, PEG/PPG/PEG phosphate, dipropylene glycol phosphate, PEG glyceryl phosphate, polybutylene glycol (PBG) phosphate, PEG cyclodextrin phosphate, PEG sorbitan phosphate, PEG alkyl sorbitan phosphate, PEG methyl glucoside phosphate, and combinations thereof.

The organophosphate may provide desired surface conditioning effects including: 1) effective desorption of undesirably adsorbed pellicle proteins, in particular those associated with tooth stain binding, calculus development and attraction of undesirable microbial species, and 2) maintaining surface conditioning effects and control of pellicle film formation for extended periods following product use. The present compositions provide a protective surface coating by binding calcium minerals within teeth (e.g., hydroxyapatite). The protective surface coating provides improved tooth surface characteristics by modifying surface hydrophilic and hydrophobic properties and improving resistance to dietary acid attack.

The amount of the organophosphate in the first composition is an effective amount to provide the protection layer for some desired time. Preferably, the protection will last for at least an hour after use of the composition. The organophosphate can be present in an amount effective to provide an increase of at least 10 degrees in water contact angle on the surface, with the hydrophobic character being maintained for a period of at least 5 minutes. In a specific embodiment, the organophosphate is present in an amount ranging from 0.01%, 0.02%, 0.03%, 0.05%, 0.07%, or 0.1% to 0.5%, 1%, 5%, 10%, 50%, or 99%, by weight, of the first composition. The amount of the organophosphate can be adjusted to provide the desired technical and sensorial benefits while mitigating any side effects which the organophosphate compound may have, for example, an undesirable bitter or soapy taste. In some medical or clinical cases when the undesirable bitter or soapy taste is not a big consideration, the amount of the organophosphate can be up to 99%, by weight, of the first composition.

In a specific embodiment, the organophosphate is defined by: R is an alkyl comprising 8 to 16 carbon atoms; a+b is from 1 to 10; and $Z^1$ and $Z^2$ are each independently selected from the group consisting of hydrogen and an alkali metal counter ion. Preferably, at least one of $Z^1$ and $Z^2$ is an alkali metal counter ion selected from the group consisting of sodium ion and potassium ion; and wherein the first composition comprises 0.01% to 10%, by weight, of the organophosphate.

Specifically, the organophosphate can be selected from the group consisting of sodium laureth-1 phosphate, sodium laureth-2 phosphate, sodium laureth-3 phosphate, sodium laureth-4 phosphate, potassium laureth-1 phosphate, sodium laureth-9 phosphate, sodium myreth-2 phosphate, sodium pareth-1 phosphate and mixtures thereof.

In a specific embodiment, the first composition comprises 0.01% or 0.05% to 5% or 10%, by weight, of sodium laureth-1 phosphate.

The pH of the first composition can be in the range from 5, 6, or 6.5 to 7.5, 8 or 10. The pH of the first composition should not be too low since there is a possibility of the organophosphate hydrolyzing in a strong acidic environment.

The Second Composition

According to the present invention, the second composition provides a source of calcium and phosphate ions for remineralization of the dental enamel or dentine by depositing into the exposed tubules, which will in turn seal, block, or occlude the tubules for a prolonged time, even permanently.

In a specific embodiment, the second composition comprises a water-insoluble calcium phosphate, wherein the water-insoluble calcium phosphate has a calcium to phosphorus molar ratio from 1:1 to 10:1.

Calcium phosphate is the main mineral found in teeth. Tooth enamel and dentine are composed of almost ninety percent of hydroxyapatite which is a calcium phosphate mineral known as bone mineral. The water-insoluble calcium phosphate as used in the present invention can release and deliver small amounts of calcium and phosphate ions under physiological conditions for promoting remineralization of the tooth enamel and dentine.

It has also been found that a specific calcium to phosphorus molar ratio range is important for tooth health and remineralization of the tooth enamel and dentine. A ratio of calcium to phosphorus that is too high may not be effective in inhibiting caries of the crowns and/or tartar on teeth, while one that is too low may not be effective in inhibiting caries near the gum and/or may increase inflammatory tendencies such as pyorrhea and gingivitis. In a specific embodiment, the water-insoluble calcium phosphate has a calcium to phosphorus molar ratio from 1:1 to 5:1, or from 1:1 to 3:1, or from 1.5:1 to 2.5:1, or from 1.3:1 to 2:1.

Suitable water-insoluble calcium phosphates useful in the present invention include, but are not limited to, apatite, calcium halide phosphate, dicalcium phosphate, tricalcium phosphate, octacalcium phosphate, and mixtures thereof. In an embodiment, the apatite is selected from the group consisting of hydroxyapatite $(Ca_{10}(PO_4)_6(OH)_2)$, fluorapatite $(Ca_{10}(PO_4)_6F_2)$, chlorapatite $(Ca_{10}(PO_4)_6Cl_2)$, bromapatite $(Ca_{10}(PO_4)_6Br_2)$ and mixtures thereof.

The water-insoluble calcium phosphate can be in any solid form, for example, substantially spherical particles, agglomerates of smaller particles, rod-like particles, needle-like particles, fibroid particles or mixtures thereof.

The water-insoluble calcium phosphate can be of any size which can deposit onto the tooth surface or into the tubules without impairing the spirit of the present invention. In a specific embodiment, the water-insoluble calcium phosphate has a particle size from 0.01, 0.5, 1, 2, or 4 to 5, 8, 10, 15 or 20 microns.

According to the present invention, the geometry and size of the water-insoluble calcium phosphate particles can be optimized so that the various tubules and even micro-cracks or crevices on the tooth surface are taken into account.

The water-insoluble calcium phosphate is present in an amount from 0.01%, 0.05%, 0.1%, 0.5%, 1%, or 2% to 3%, 5%, 10%, 20%, 50%, or 99%, by weight, of the second composition. In a specific embodiment, the second composition comprises 0.1% to 20%, by weight, of apatite. In a further specific embodiment, the second composition comprises 1% to 5%, by weight, of hydroxyapatite. The amount of the water-insoluble calcium phosphate can be adjusted to provide the desired technical and sensorial benefits while mitigating any side effects. In some medical or clinical cases when the side effects do not matter much, the amount of the water-insoluble calcium phosphate can be up to 99%, by weight, of the second composition.

The pH of the second composition can be in the range from 6, 7, or 8 to 9, 10, or 11. The pH can be achieved through a proper balancing of the calcium phosphate sources or by addition of an alkaline or acidic agent. Without wishing to be bound by theory, a relatively basic pH is preferred because it is believed to stabilize the water-insoluble calcium phosphate from being dissolved.

Optional Components

The first composition and the second composition of the present invention can each independently contain a variety of optional conventional components useful in oral compositions to increase the benefits mentioned herein or provide additional benefits. Such optional components include, but are not limited to, a fluoride ion source, a thickening agent, a humectant, a surfactant, an antibacterial agent, a colorant, a flavorant, and some other conventional components.

A fluoride ion source, also called a water-soluble fluoride source, capable of providing free fluoride ions, can help accelerating remineralization by increasing local supersaturation with respect to fluoridated calcium phosphate deposition. Fluoride uptake or fluoridation refers to the acquisition of fluoride into tooth substrates resulting from topical treatments with fluoride agents. Teeth with increased remineralization and fluoride uptake exhibit superior resistance to acid demineralization and therefore help prolong the protective effect on the tooth surface. The water-soluble fluoride source can be selected from the group consisting of sodium fluoride, stannous fluoride, sodium monofluorophosphate, amine fluoride, and mixtures thereof. In a specific embodiment, the first composition comprises a water-soluble fluoride source capable of providing from 50 ppm, 500 ppm, 1000 ppm, or 1500 ppm to 2000 ppm, 2500 ppm, 3000 ppm, or 3500 ppm of free fluoride ions. In a further specific embodiment, the first composition comprises from 0.005%, 0.01%, or 0.02% to 0.1%, 1%, or 5%, by weight, of sodium fluoride. In an even further specific embodiment, the first composition comprises 0.05% to 5%, by weight, of sodium laureth-1 phosphate and 0.01% to 1%, by weight, of sodium fluoride, and the second composition comprises 1% to 5%, by weight, of hydroxyapatite.

Thickening agents, also called thickeners, are generally used to increase the viscosity of a solution or liquid/solid mixture. According to the present invention, thickening agents can be incorporated to provide a consumer desirable consistency and tooth coating ability by adjusting the viscosity of the composition. The oral care composition of the present invention can have a viscosity ranging from 10 cps, 50 cps, 100 cps, 500 cps, 800 cps, 1200 cps, or 2000 cps to 3000 cps, 5000 cps, 8000 cps, 12000 cps, 20000 cps, 30000 cps, or 45000 cps, depending on the delivery form of the composition. In a specific embodiment, the first composition has a viscosity of 1200 cps to 3000 cps. In another specific embodiment, the second composition has a viscosity of 2000 cps to 8000 cps. Thicker composition tends to provide longer lasting benefits on the tooth surface. Thickening agents may also improve the suspension of insoluble ingredients to provide a stable and uniform composition. This is especially advantageous when the second composition comprising the water-insoluble calcium phosphate is a mouth rinse. Preferred thickening agents are selected from the group consisting of carboxyvinyl polymers, carrageenan, xanthan gum, cellulosic polymers, hydroxyethyl cellulose, carboxymethyl cellulose, ammonium acryloyldimethyltaurate/vinylprrolidone copolymer, polyethylene oxide, acrylates/C10-30 alkyl acrylate crosspolymer, polyacrylic acid, cross-linked polyacrylic acid, polycarbophil, alginate, clay, glucose, pectin, gelatin, and combinations thereof. Colloidal magnesium aluminum silicate or finely divided silica can also be used as part of the thickening agent to further improve texture. The thickening agent can be present in an amount from 0.01%, 0.1%, 0.2%, 0.3%, or 0.4% to 2%, 5%, 8%, 10%, or 20%, by weight, of the first composition or the second composition.

Humectants such as polyethylene glycols can also been used to modify viscosity and to provide a smooth feel to dentifrice compositions. Polyethylene glycols are available in a large range of average molecular weights and have different properties depending upon their average molecular weights. The humectant serves to keep the oral composition, especially a toothpaste composition, from hardening upon exposure to air and give a moist feel to the mouth. Certain humectants can also impart a desirable sweet flavor to oral compositions such as mouth rinse and toothpaste. Suitable humectants for use in the present invention include edible polyhydric alcohols such as glycerin, sorbitol, xylitol, butylene glycol, polyethylene glycol, propylene glycol, and mixtures thereof. The humectant is optionally present in an amount of 1%, 2%, 5%, or 8% to 15%, 25%, 50%, or 70%, by weight, of the first composition or the second composition.

Surfactants are useful, for example, to make other components of the oral care composition more compatible with one another. This provides enhanced stability, helps in cleaning the dental surface through detergency, and provides foam upon agitation, e.g., during brushing with a dentifrice composition of the invention. Any orally acceptable surfactant, most of which are anionic, nonionic or amphoteric, can be used. Suitable anionic surfactants include without limitation water-soluble salts of C8-20 alkyl sulfates, sulfonated monoglycerides of C8-20 fatty acids, sarcosinates, taurates and the like. Illustrative examples of these and other classes include sodium lauryl sulfate, sodium coconut monoglyceride sulfonate, sodium lauryl sarcosinate, sodium lauryl isoethionate, sodium laureth carboxylate and sodium dodecyl benzenesulfonate. Suitable nonionic surfactants include without limitation poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include without limitation derivatives of C8-20 aliphatic secondary and tertiary amines having an anionic group such as carboxylate, sulfate, sulfonate, phosphate or phosphonate. A suitable example is cocoamidopropyl betaine. The surfactant is optionally present in an amount of 0.01%, 0.05%, or 0.1% to 2%, 5%, or 10%, by weight, of the first composition or the second composition.

Antibacterial agents useful in the present invention include, but are not limited to, water insoluble, non-cationic antibacterial agents and water soluble antibacterial agents such as quaternary ammonium salts and bis-biquanide salts. Triclosan monophosphate is an additional water soluble antibacterial agent. In some preferred embodiments, the antibacterial agent is selected from the group consisting of cetylpyridinium halide, domiphen halide, a stannous ion source, a zinc ion source, a copper ion source, and mixtures thereof. These antibacterial agents may be present at levels of from 0.01%, 0.05%, 0.1%, or 0.2% to 0.5%, 1.0%, 1.2% or 1.5%, by weight, of the first composition or the second composition.

Colorants herein include pigments, dyes, lakes and agents imparting a particular luster or reflectivity such as pearling agents. A colorant can serve a number of functions, including for example, to provide a white or light-colored coating on a dental surface, to act as an indicator of locations on a dental surface that have been effectively contacted by the composition, and/or to modify appearance, in particular color and/or opacity, of the composition to enhance attractiveness to the user. Any orally acceptable colorant can be used, including but not limited to talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride and the like.

Flavorants are useful for example to enhance taste of the composition. Any orally acceptable natural or synthetic flavorant can be used, including but not limited to vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants and the like. Also encompassed within flavorants herein are ingredients that provide fragrance and/or other sensory effect in the mouth, including cooling or warming effects. Such ingredients illustratively include menthol, menthyl acetate, menthyl lactate, camphor, eucalyptus oil, eucalyptol, anethole, eugenol, cassia, oxanone, α-irisone, propenyl guaiethol, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), menthone glycerol acetal (MGA) and the like.

Oral Care Kit and Product

The present invention also provides any form of kit and product comprising the first composition and the second composition as discussed above.

In some embodiments, the oral care kit comprises:

(a) a first product containing a first composition, wherein the first composition comprises 0.01% to 99%, by weight, of an organophosphate as defined above;

(b) a second product containing a second composition, wherein the second product is a mouth rinse with a pH from 7 to 10 and a viscosity from 2000 cps to 8000 cps, and wherein the second composition comprises 0.01% to 99%, by weight, of a water-insoluble calcium phosphate having a calcium to phosphorus molar ratio from 1:1 to 10:1 and (c) instructions instructing a user to first use the first product to contact a tooth surface and thereafter immediately use the second product to contact the tooth surface.

In some embodiments, the kit further includes an applicator to apply the first and/or second compositions to the tooth surface, for example, a syringe-type applicator for depositing a composition on the tooth surface or an applicator in the shape of a semicircular trough for use in applying composition to the tooth surface. The kit may also optionally include instructions on the use of an applicator in applying the composition to a tooth surface.

In a specific embodiment, the first product and the second product can be physically separated, each independently as any suitable form, for example, as a liquid form or a dry powder. When the composition provided is a dry powder, the composition may be reconstituted by the addition of a suitable solvent, which may also be included in the kit. In embodiments where a liquid form is provided, the composition may be concentrated or ready to use.

In a specific embodiment, the first product and the second product are each independently a mouth rinse.

In some embodiments, the present invention intends to provide a single oral care product comprising a first container and a second container, wherein the first container contains a first composition comprising 0.01% to 99%, by weight, of an organophosphate as defined above; and wherein the second container contains a second composition comprising 0.01% to 99%, by weight, of a water-insoluble calcium phosphate which has a calcium to phosphorus molar ratio from 1:1 to 10:1. The product may optionally contain instructions instructing a user to dispense the first composition before the second composition is dispensed.

In a specific embodiment, the single oral care product further comprises instructions instructing a user to first dispense the first composition from the first container to contact a tooth surface and thereafter dispense the second composition from the second container to contact the tooth surface for every use.

In another specific embodiment, the single oral care product further comprises a pump which pumps the first composition from the first container upon a first actuation and pumps the second composition from the second container upon a second actuation for every treatment regimen use.

EXAMPLES

The following examples further describe and demonstrate embodiments within the scope of the present invention. These examples are given solely for the purpose of illustration and are not meant to be construed as limitations of the present invention, as many variations thereof are possible without departing from the spirit and scope of the present invention.

The first composition

Table 1 shows examples of the first composition according to the present invention in the form of mouth rinses. The preparation process is as follows: add glycerin and polymers to a first mixing vessel, mixing until well dispersed to get Premix 1; add water (10% of the total amount), flavors & sensates, sweeteners, liquid preservatives, surfactants, and colorants & aesthetics to a second mixing vessel, mixing until well dispersed and homogenous to get Premix 2; add sodium fluoride, organophosphate, water (90% of the total amount), solid preservatives, and thickening agents to a main mixing tank, mixing until homogenous to get a main mix; add Premix 1 to the main mix, mixing until well dispersed; add 25% of the total sodium hydroxide (if applicable) to the main mix, mixing until homogenous; add Premix 2 to the main mix, mixing until well dispersed and homogenous; and add the rest of the sodium hydroxide until the pH is 7.

TABLE 1

| Ingredients | A1 | A2 | A3 | A4 | A5 | A6 | A7 |
|---|---|---|---|---|---|---|---|
| Water | 80.014 | 80.144 | 79.914 | 79.729 | 79.364 | 79.794 | 79.704 |
| Glycerin | 18.000 | 18.000 | 18.000 | 18.000 | 18.000 | 18.000 | 18.000 |
| Methylparaben | 0.020 | 0.020 | 0.020 | 0.020 | 0.020 | 0.020 | 0.020 |
| Propylparaben | 0.005 | 0.005 | 0.005 | 0.005 | 0.005 | 0.005 | 0.005 |
| Benzyl Alcohol | 1.000 | 0.900 | 1.000 | 0.900 | 0.800 | 0.900 | 0.900 |
| Aristoflex AVC | 0.400 | — | 0.500 | — | — | — | — |
| Carbopol ETD2020 | — | 0.150 | — | 0.150 | 0.350 | 0.200 | 0.175 |
| Polyox WSR1105 | — | — | — | 0.200 | 0.150 | 0.200 | 0.200 |
| Vitamin E Acetate | — | 0.070 | — | 0.070 | 0.070 | 0.070 | 0.070 |
| Sodium Fluoride | — | 0.050 | — | 0.020 | 0.050 | 0.050 | 0.020 |
| MAP L213S[1] | 0.330 | — | 0.330 | — | 0.660 | — | 0.330 |
| Foamphos L-9[2] | — | 0.330 | — | 0.330 | — | 0.330 | — |
| Sodium Saccharin | 0.013 | 0.013 | 0.013 | 0.013 | 0.013 | 0.013 | 0.013 |
| Sucralose | 0.008 | 0.008 | 0.008 | 0.008 | 0.008 | 0.008 | 0.008 |
| Peppermint 92 180 Blend | 0.100 | — | 0.100 | 0.100 | 0.100 | — | 0.100 |
| Starburst Peppermint | — | — | — | — | — | 0.100 | — |
| Polar Mint Diluted | — | — | — | 0.120 | — | — | 0.120 |
| Sodium Hydroxide | — | 0.200 | — | 0.200 | 0.200 | 0.200 | 0.200 |
| Titanium Dioxide | 0.100 | 0.100 | 0.100 | 0.050 | 0.100 | 0.100 | 0.050 |
| Candurin Silver Lustre | — | — | — | 0.075 | — | — | 0.075 |
| Timica Extra Bright | — | — | — | — | 0.100 | — | — |
| Poloxamer 407 | 0.010 | 0.010 | 0.010 | 0.010 | 0.010 | 0.010 | 0.010 |
| Total | 100 | 100 | 100 | 100 | 100 | 100 | 100 |

[1] Laureth-1 phosphate supplied by Rhodia, pre-neutralized
[2] Laureth-9 phosphate supplied by Alzo, neutralized with NaOH The first compositions, A3 to A7, have a viscosity of 3072 cps, 1376 cps, 216.5 cps, 1408 cps, and 2616 cps, respectively. A1 and A2 are not measured.

Table 2 shows examples of the first composition according to the present invention in the form of toothpastes. The preparation process is as follows: add water, humectants, part of flavor, colorant, buffer and active to a main mixing tank of 35° C., mixing well and ensuring all the ingredients have dissolved or been well dispersed; add organophosphate, thickening agents and sweetener into the main mixing tank, mixing and homogenizing until well dispersed and homogeneous; add abrasives, mixing and homogenizing until well dispersed and homogeneous; deaerate; add surfactant solution, rest part of flavor to the main mixing tank, mixing and homogenizing until homogeneous; de-aerate; pump out and cool the batch to less than 40° C.

TABLE 2

| Ingredients | A8 | A9 | A10 | A11 | A12 |
|---|---|---|---|---|---|
| Sorbitol solution (70%) | 22.169 | 40.370 | 40.500 | — | 23.000 |
| Sodium fluoride | 0.321 | 0.234 | — | — | — |
| Water purified | 45.000 | 33.096 | 22.950 | — | 44.170 |
| Silica abrasive | 15.000 | 12.500 | 17.000 | 17.000 | 15.000 |
| Sodium Lauryl Sulfate (28%) | 7.000 | 5.000 | 5.000 | 3.500 | 5.000 |
| Sodium Carboxymethyl Cellulose | 1.400 | 1.300 | 1.300 | — | 1.500 |
| Carrageenan | — | 0.700 | 0.700 | 0.600 | — |
| Carbomer 956 | 0.400 | — | — | — | 0.500 |
| Sodium saccharin | 0.280 | 0.300 | 0.300 | 0.300 | 0.280 |
| Xanthan gum | 0.250 | — | — | 0.250 | 0.250 |
| Titanium dioxide | 0.250 | 0.500 | 0.525 | 0.400 | 0.250 |
| Flavor | 0.900 | 1.000 | 0.900 | 1.000 | 1.000 |
| Sodium hydroxide 32% | 3.750 | — | — | — | 3.750 |
| Mica | 0.280 | — | — | 0.500 | 0.300 |
| MAP L-130[3] | 3.000 | — | — | — | — |
| Foamphos L-3[4] | — | 5.000 | — | — | — |
| MAP 230K[5] | — | — | 10.000 | — | — |
| DLP-10[6] | — | — | — | 7.500 | — |
| Crodaphos SG[7] | — | — | — | — | 5.000 |
| Glycerin | — | — | — | 41.950 | — |
| Sodium polyphosphate | — | — | — | 13.000 | — |
| Sodium citrate | — | — | 0.150 | — | — |
| Sodium gluconate | — | 1.064 | — | — | — |
| Zinc citrate | — | 0.955 | 0.375 | — | — |
| Hydroxyethyl Cellulose | — | 0.300 | 0.300 | — | — |
| Stannous chloride | — | 1.160 | — | — | — |
| Propylene glycol | — | — | — | 7.000 | — |
| Polyethylene glycol | — | — | — | 7.000 | — |
| Total | 100 | 100 | 100 | 100 | 100 |

[3] Laureth-3 phosphate supplied by Rhodia, neutralized with NaOH
[4] Laureth-3 phosphate supplied by Alzo, neutralized with NaOH
[5] Potassium C12/13 phosphate supplied by Croda
[6] Sodium diLaureth-10 phosphate supplied by Nikkol Chemical
[7] PPG5 Ceteareth-10 phosphate supplied by Croda, neutralized with NaOH The second composition Table 3 shows examples of the second composition according to the present invention in the form of mouth rinses. The preparation process is the same as that for the first compositions in the form of mouth rinses, except that hydroxyapatite is added in the Premix 2 and that the main mix does not include sodium fluoride and organophosphate.

TABLE 3

| Ingredients | B1 | B2 | B3 | B4 | B5 | B6 | B7 | B8 |
|---|---|---|---|---|---|---|---|---|
| Water | 77.744 | 77.674 | 75.244 | 79.244 | 76.279 | 78.404 | 77.654 | 79.154 |
| Glycerin | 18.000 | 18.000 | 18.000 | 18.000 | 18.000 | 18.000 | 18.000 | 18.000 |
| Methylparaben | 0.020 | 0.020 | 0.020 | 0.020 | 0.020 | 0.020 | 0.020 | 0.020 |
| Propylparaben | 0.005 | 0.005 | 0.005 | 0.005 | 0.005 | 0.005 | 0.005 | 0.005 |
| Benzyl Alcohol | 1.000 | 0.900 | 1.000 | 1.000 | 0.900 | 0.900 | 0.900 | 0.900 |
| Aristoflex AVC | 0.500 | — | 0.500 | 0.500 | — | — | — | — |
| Carbopol ETD2020 | — | 0.200 | — | — | 0.250 | 0.125 | 0.125 | 0.125 |
| Polyox WSR1105 | — | 0.200 | — | — | 1.000 | 0.500 | 0.500 | 0.500 |
| Vitamin E Acetate | — | 0.070 | — | — | 0.070 | 0.070 | 0.070 | 0.070 |
| Bio-Gel HTP[8] | 2.500 | — | 5.000 | 1.000 | — | — | — | — |
| nanoXIM.Care powder[9] | — | 2.500 | — | — | 3.000 | 1.500 | 2.250 | 0.750 |
| Sodium Saccharin | 0.013 | 0.013 | 0.013 | 0.013 | 0.013 | 0.013 | 0.013 | 0.013 |
| Sucralose | 0.008 | 0.008 | 0.008 | 0.008 | 0.008 | 0.008 | 0.008 | 0.008 |
| Peppermint 92 180 Blend | 0.100 | — | 0.100 | 0.100 | — | — | — | — |
| Starburst Peppermint | — | 0.100 | — | — | 0.120 | 0.120 | 0.120 | 0.120 |
| Sodium Hydroxide | — | 0.200 | | | 0.200 | 0.200 | 0.200 | 0.200 |
| Titanium Dioxide | 0.100 | 0.100 | 0.100 | 0.100 | 0.050 | 0.050 | 0.050 | 0.050 |
| Poloxamer 407 | 0.010 | 0.010 | 0.010 | 0.010 | 0.010 | 0.010 | 0.010 | 0.010 |
| Candurin Silver Lustre | — | — | — | — | 0.075 | 0.075 | 0.075 | 0.075 |
| Total | 100 | 100 | 100 | 100 | 100 | 100 | 100 | 100 |

[8] Hydroxyapatite supplied by Bio-Rad, Hercules, CA, USA
[9] Hydroxyapatite supplied by Fluidinova, Moreira da Maia, Portugal As a mouth rinse, appropriate viscosity will suspend the hydroxyapatite uniformly in the composition and facilitate proper contact and retention of the composition on the tooth surface. The second compositions, B1 to B8, have a viscosity of 2580 cps, 7690 cps, 5072 cps, 2600 cps, 29433 cps, 132 cps, 220 cps, and 116 cps, respectively.

Table 4 shows examples of the second composition according to the present invention in the form of nonabrasive tooth gels. The preparation process is as follows: add mineral oil/petrolatum/Versagel, humectants, part of flavor, and colorant to a main mixing tank of 35° C., mixing well and ensuring all the ingredients have dissolved or been well dispersed; add hydroxyapatite and sweetener into the main mixing tank, mixing and homogenizing until well dispersed and homogeneous; de-aerate; add surfactant solution, rest part of flavor to the main mixing tank, mixing and homogenizing until homogeneous; de-aerate; pump out and cool the batch to less than 40° C.

TABLE 4

| Ingredients | B9 | B10 | B11 | B12 | B13 |
|---|---|---|---|---|---|
| Bio-Gel HTP[8] | 13.330 | — | — | 5.000 | 2.000 |
| nanoXIM.Care powder[9] | — | 8.000 | 10.000 | — | — |
| Glycerin | 20.000 | 13.000 | 22.000 | 35.000 | — |
| Flavor | 2.000 | 2.000 | 2.000 | 2.000 | 1.000 |
| Saccharin | 0.500 | 0.500 | 0.500 | 0.500 | 2.000 |
| Polyethylene oxide | 2.000 | 2.000 | 2.000 | 2.000 | — |
| Carbomer 956 | 0.500 | 0.500 | 0.500 | 0.500 | — |
| Mineral Oil | — | — | — | 55.000 | — |
| Petrolatum | 61.670 | 64.000 | 63.000 | — | — |
| Versagel | — | — | — | — | 95.000 |
| Total | 100 | 100 | 100 | 100 | 100 |

[8] Hydroxyapatite supplied by Bio-Rad, Hercules, CA, USA
[9] Hydroxyapatite supplied by Fluidinova, Moreira da Maia, Portugal Sequential application system One of the first compositions as shown in Tables 1 and 2 and one of the second compositions as shown in Tables 3 and 4 can be combined into a sequential oral application treatment regimen. Examples of sequential compositions according to the present invention are shown in Table 5.

TABLE 5

| | Ex. 1 | Ex. 2 | Ex. 3 | Ex. 4 | Ex. 5 | Ex. 6 | Ex. 7 |
|---|---|---|---|---|---|---|---|
| The first composition | A6 | A8 | A1 | A10 | A3 | A7 | A12 |
| The second composition | B2 | B3 | B5 | B7 | B9 | B11 | B12 |

The compositions in the form of mouth rinses are applied to the tooth surface by swishing and gargling 20 ml of the mouth rinse in the mouth for 30 seconds and then spitting out. In the application where the subject composition is too viscous or too thick to be swished or gargled in the mouth, suitable applicators such as a swab can be used to apply (e.g., spread or daub) the composition onto the tooth surface.

The compositions in the form of toothpastes are applied to the tooth surface by brushing with a toothbrush for 2 minutes.

The compositions in the form of tooth gels are applied to the tooth surface by applying the gels evenly into a mouth tray and putting the mouth tray onto the teeth for 10 minutes.

Efficacy measurement

Quartz Crystal Microbalance with Dissipation monitoring (QCM-D)

QCM-D is a very sensitive mass balance technique allowing simultaneous measurement of adsorption kinetics and viscoelastic properties of an adsorbing layer.

In QCM-D, a quartz crystal is excited to oscillate at its fundamental resonant frequency by the application of an AC voltage across the crystal. A material adsorbed onto the surface of the crystal causes the resonant frequency to change, which is proportional to the mass of the adsorbed film.

The damping/dissipation of the crystal's oscillation by the film can be measured, allowing for the determination of the viscoelasticity of the film.

$$\Delta D = E_{dissipation}/2\pi E_{stored}$$

wherein D is the energy dissipated per oscillation divided by the total energy stored in the crystal.

A large value for $\Delta D$ indicates that a soft, easily deformed material is attached to the crystal. A rigid material leads to a small $\Delta D$.

FIGS. 1(a) to 1(e) show the QCM-D data for a tooth surface treated with Ex. 1 of the present invention.

Three steps, in sequential order, are followed to treat the test tooth surface. The first step is to rinse the tooth surface with deionized water. The second step is to rinse the tooth surface with the first composition, A6. The third step is to further rinse the tooth surface with the second composition, B2. The three columns in each of FIGS. 1(a) to 1(e) represent the QCM-D test results after each step.

It can be seen from the QCM-D data that, before the treatment according to the present invention, no adsorbed layer is formed on the tooth surface. After treatment with the first composition, A6, a layer displaying viscoelastic properties is adsorbed onto the tooth surface. After further treatment with the second composition, B2, the adsorbed layer is strengthened by increased mass and becomes much thicker. The decrease in density and viscosity indicates that the deposition of the hydroxyapatite from the second composition, B2, is in a discrete way instead of forming a continuous hydroxyapatite layer.

Dentine Tubule Occlusion

Dentine tubule occlusion measures the degree to which a product can occlude the tubules present in dentine. This can be correlated to the degree of hypersensitivity relief that a product can deliver—the greater the level of tubule occlusion, the greater the sensitivity relief. In-vitro tubule occlusion brushing assay (TUBA) evaluation is carried out to evaluate the onset and durability of dentine tubule occlusion when the dentine samples are treated according to the present invention. Light microscope images are taken of the dentine samples before and after treatment.

The evaluation procedure includes the following steps:
1. Three 0.8 mm thick coronal dentine slabs are sanded with 20μ lapping paper and then polished with 9μ lapping paper.
2. The polished slabs are etched in 15 ml 6% citric acid for 1 minute, sonicated in deionized (DI) water for 3 minutes, and then placed in a pooled saliva bath for 1 hour to aid in pellicle formation, imaged through light microscope at 500×.
3. A pea-sized portion of an Oral B® Pro-Expert toothpaste (produced on Mar. 18, 2011 in the US) is applied to each etched slab. An Oral-B® power brush & sensitive tip (Oral-B® Triumph 5000 wireless smart-guide powerbrush, manufactured by Braun GmbH in Germany in 2009) is used to brush the slabs with the applied toothpaste. The toothpaste is reapplied every 30 seconds for 1 minute. Place the slabs in a dose cup containing 15 ml saliva and let sit for at least 60 minutes. Rinse the slabs in DI water and store in DI water until imaging. Image through the same light microscope at 500×.
4. Randomly allocate the three slabs to three treatment regimens: immersed in DI water for 3 minutes, immersed in the first composition A6 for 1.5 minutes followed by the second composition B2 for 1.5 minutes, and immersed in the second composition B2 for 1.5 minutes followed by the first composition A6 for 1.5 minutes. Image through the same light microscope at 500×. Repeat for 5 cycles.
5. The slabs are further rotated in pooled saliva for 16 h, and then etched in 15 ml acid (Regular Coca-Cola® or 1% citric acid) for several minutes, imaged through the same light microscope at 500×.
6. Images are graded by trained panels to give Tubule Occlusion Score (TOS) on a 6-point histomorphological scale: 0 for 100% tubules open, 1 for 90% tubules open, 2 for 50% tubules open, 3 for most tubules occluded while outlines visible, 4 for few tubules visible, 5 for no open tubules. The grade scores are then analyzed by one-way ANOVA (Analysis of Variance).

Figure 1A:
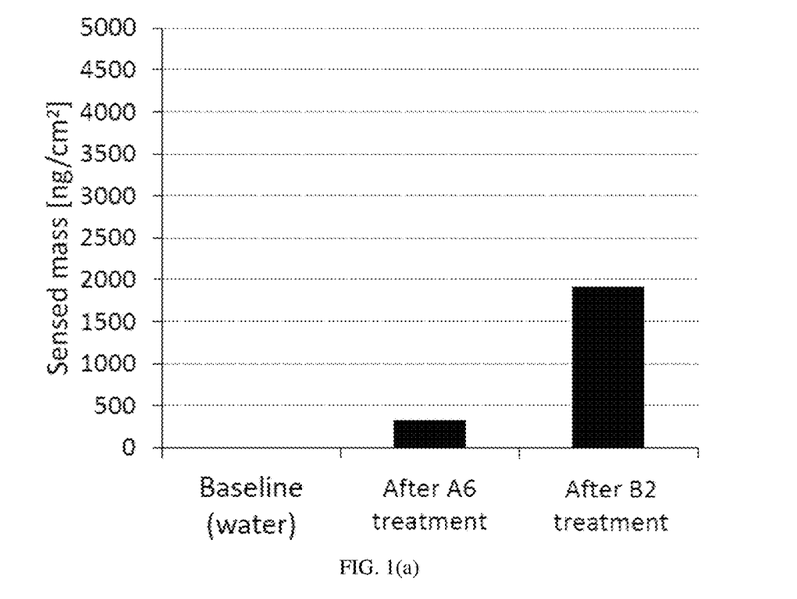
FIGS. 1(a) to 1(e) show property analyses of a tooth surface by Quartz Crystal Microbalance with Dissipation monitoring (QCM-D) when the tooth surface is treated according to a specific embodiment of the present invention.
Figure 1B:
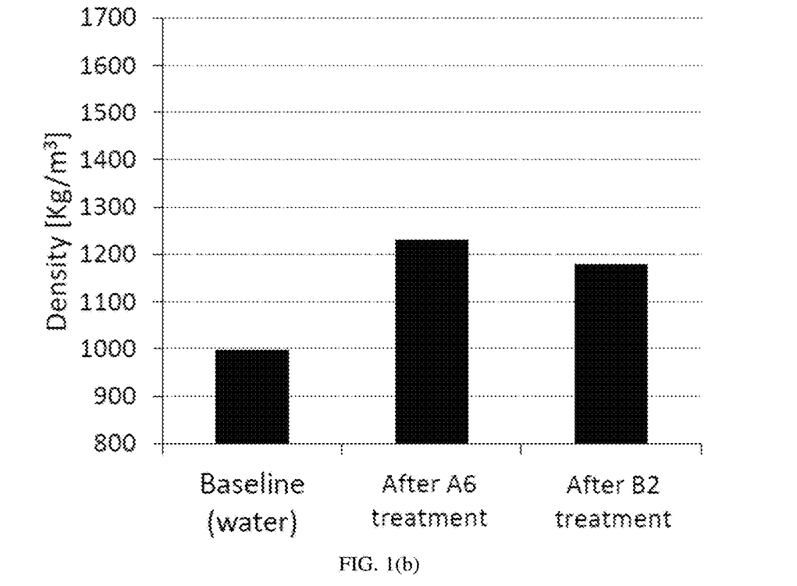
Figure 1C:
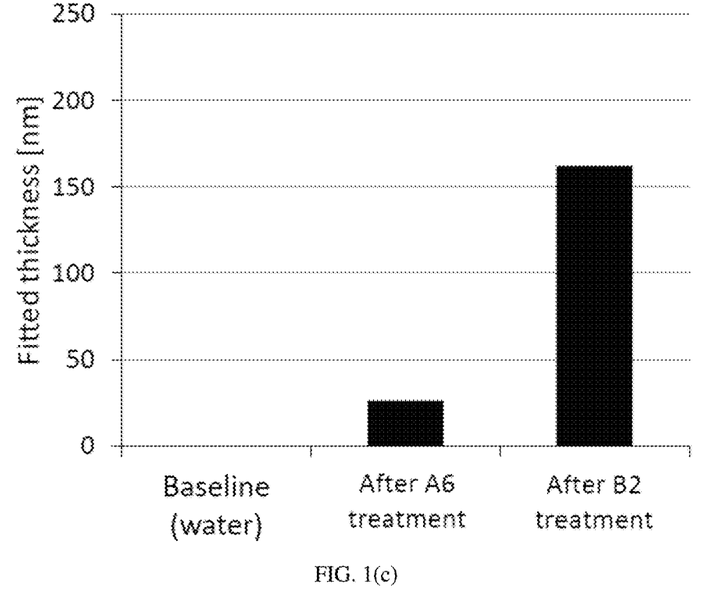
Figure 1D:
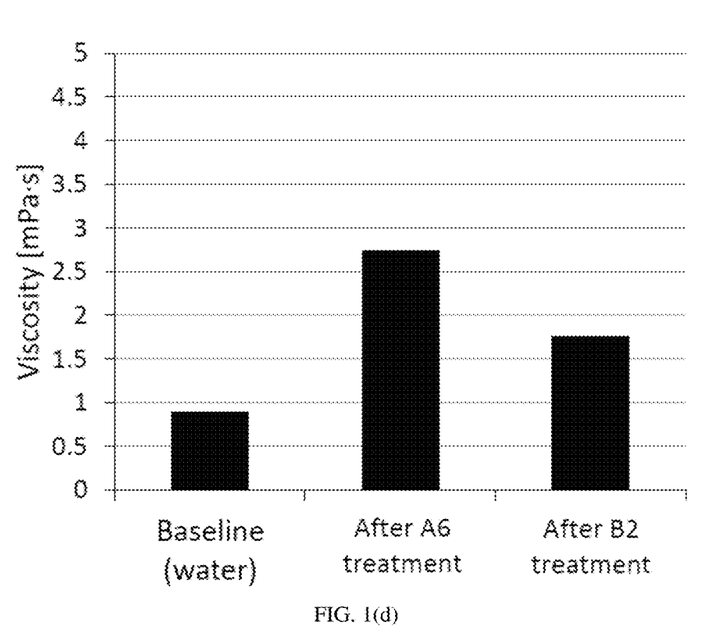
Figure 1E:
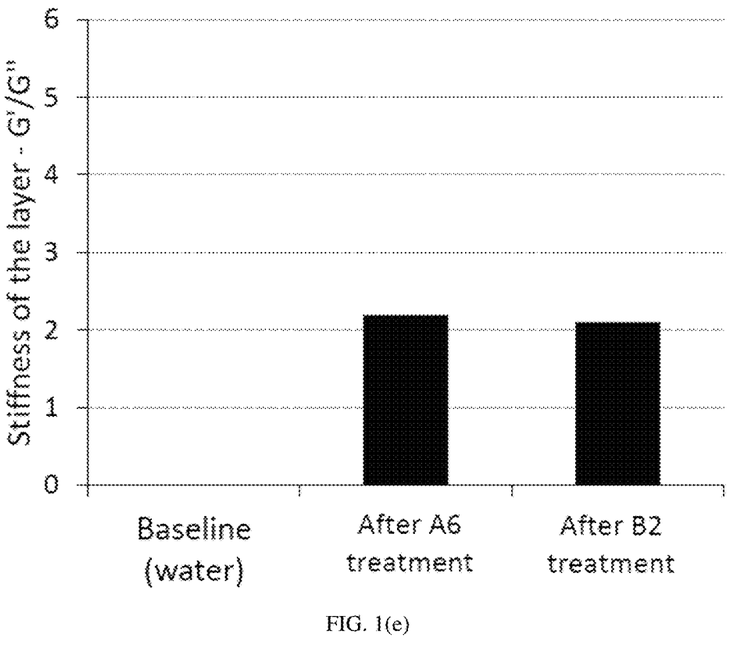
Figure 2:
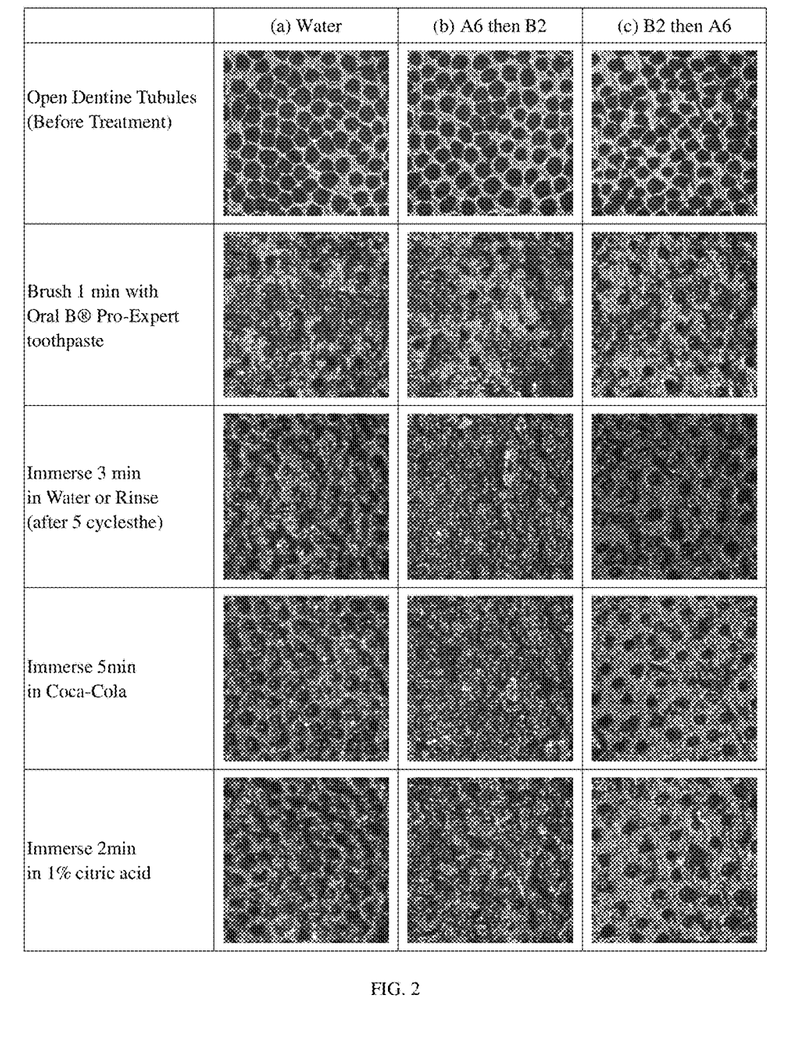
FIG. 2 shows light microscope images of dentine samples under three treatment regimens.

FIG. 2 shows some representative images taken during the evaluation procedure. Column (a) illustrates the evolution of the tubule occlusion when the slab is treated with water. Column (b) illustrates the evolution of the tubule occlusion when the slab is treated with the sequential system according to the present invention, that is, the first composition A6 followed by the second composition B2. Column (c) illustrates the evolution of the tubule occlusion when the slab is treated with a sequential system opposite to the present invention, that is, the second composition B2 followed by the first composition A6.

It can be seen from FIG. 2 that a smear layer is formed after brushing with the Oral B® Pro-Expert toothpaste but there are still some tubules open and exposed. The Oral B® Pro-Expert toothpaste does not contain the first composition or the second composition as defined in the present invention. When the sequential system according to the present invention is applied for 5 cycles, almost no open tubules can be observed. Even after mechanical and acid challenges (step 5 above), almost no or only few open tubules can be observed.

In comparison, when water is applied after the brushing, the smear layer seems to be reorganized and more open tubules are exposed. After mechanical and acid challenges, the smear layer almost disappears and even more open tubules become exposed.

As a further comparison, when an opposite sequence of the present sequential system is applied, that is, treatment with B2 followed by A6, there seems to be a new layer formed on the smear layer. The new layer makes the dentine surface smoother but the tubules still remain to be open and exposed. After mechanical and acid challenges, more open tubules become exposed.

The TOS results indicate that the treatment with A6 followed by B2 is better than the treatment with water and the treatment with water is better than the treatment with B2 followed by A6, in terms of acid-resistant dentine occlusion.

Remineralization

Further exploratory studies are conducted to demonstrate the ability of the sequential system of the present invention to remineralize the enamel or dentine and inhibit the demineralization of remineralized enamel or dentine, using the widely applied pH cycling model.

Four enamel samples are prepared by cutting 4-mm cores from extracted, bovine teeth using a diamond core drill. Approximately 50 microns of the outer enamel is removed by polishing with 600 grit silicon carbide-water slurry. The samples are further polished for 90 minutes with gamma alumina (Linde No. 3, AB Gamma Polishing Alumina) to a high finish. Enamel samples found to have surface imperfections are rejected. Demineralized enamel samples are then prepared by placing in 25 ml of a solution containing 0.1M/1 lactic acid, and 0.2% Carbopol 907 (B.F. Goodrich, Co.) 50% saturated with respect to hydroxyapatite (HAP), pH 5.0 for 72 hours at 37° C. Lesions formed from this procedure are generally 60-80 microns in depth. After demineralization, samples are thoroughly rinsed with deionized, distilled water.

The four samples are randomly allocated to four treatment regimens: (a) brush 2 mins with Oral B® Pro-Expert toothpaste+immerse in A6 for 2 mins+immerse in B2 for 2 mins; (b) brush 2 mins with Oral B® Pro-Expert toothpaste+immerse in B2 for 2 mins+immerse in A6 for 2 mins; (c)

brush 2 mins with Oral B® Pro-Expert toothpaste; and (d) immerse in DI water for 2 mins.

Each sample is placed in 20 ml of fresh, pooled human saliva for 12 hours to form an initial layer of pellicle on the demineralized enamel surfaces, and then follows the pH cycling procedure: Treatment→Saliva remineralization for 1 hour→Treatment→Saliva remineralization for 1 hour→Demineralization in 25 ml of fresh demineralization solution of the same composition used to form the initial lesions for 3 hours→Saliva remineralization for 1 hour→Treatment→Saliva remineralization for 1 hour→Treatment→Saliva overnight. Repeat the pH cycling procedure for 7 days.

Calcium (Ca) uptake analyses are done on the four enamel samples upon completion of seven days of treatment using the "microdrill biopsy" technique. All of the samples necessary for Ca analyses are taken from an enamel sample that is milled to a total depth of 100 microns into the enamel in order to assure penetration through the initial lesion. Ca analysis is done before the cycling treatment (as initial Ca) and after cycling treatment (as after-treatment Ca), then Ca uptake is calculated by subtracting the initial Ca from the after-treatment Ca.

Figure 3:
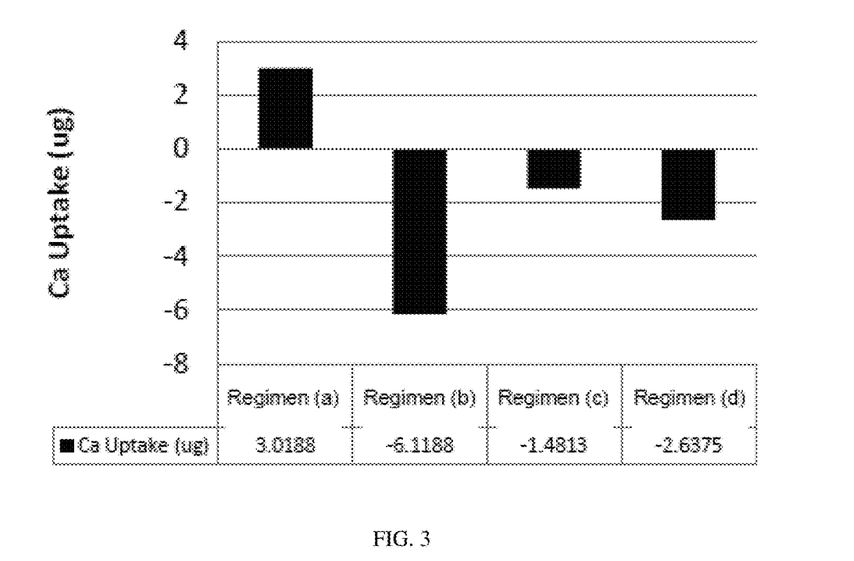
FIG. 3 shows calcium uptake analysis results for four treatment regimens.

FIG. 3 illustrates the calcium uptake analysis results for the four treatment regimens. The regimen (a) according to the present invention shows a directionally higher calcium uptake versus the other 3 treatment regimens.

After the Ca uptake analysis, half of each sample surface that has been subjected to remineralization treatment is covered with nail polish. The portion which remains uncovered is then submitted to a new cycle of demineralization by acid treatment in a bath containing 8 ml of demineralization solution, for 48 hours at 37° C. Following the acid challenge, enamel samples are cut plano-parallel using a hard tissue sectioning saw. Each section is cut to allow the control, treated, and acid challenge portion to be represented for microradiographic analysis. Standard black and white film developing methods are used. Radiographs are analyzed using Transverse Microradiography. Mineral profile scans are made from the areas of interest (control, remineralized, acid challenged). Analysis of the lesion body, known as the $\Delta Z$ for each area, is calculated as the difference between sound enamel and the lesion. The change in $\Delta Z$ from the initial lesion to the lesion exposed to the pH cycling treatments is recorded as the remineralization value. The difference between $\Delta Z$ in the acid challenged area and $\Delta Z$ in the initial lesion is the acid resistance value.

Figure 4:
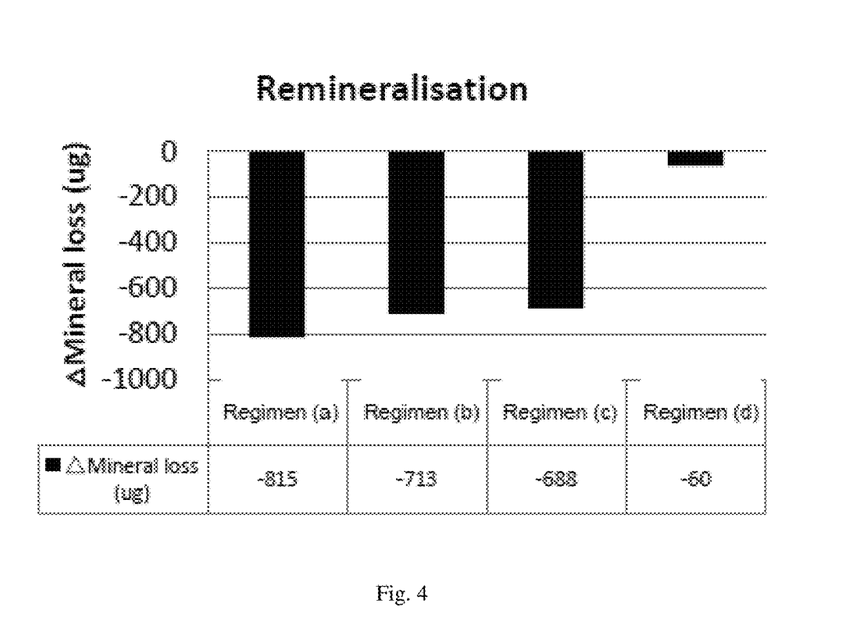
FIG. 4 shows remineralization values of microradiographic analysis for four treatment regimens.
Figure 5:
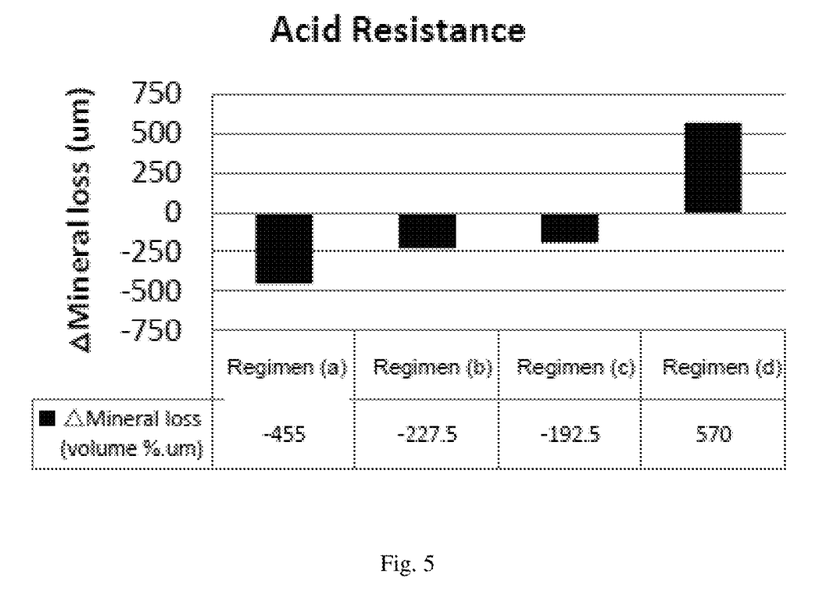
FIG. 5 shows acid resistance values of microradiographic analysis for four treatment regimens.

FIGS. 4 and 5 illustrate the remineralization values and the acid resistance values for the four treatment regimens, respectively. The larger the negative value of the ΔMineral loss, the better remineralization and acid resistance efficacy. The regimen (a) according to the present invention shows the best efficacy among the four treatment regimens.

Therefore, in combination with the TUBA images discussed hereinbefore, it can be assumed that the sequential system according to the present invention can remineralize the dental enamel or dentine by depositing into the exposed tubules, and therefore seal, block, or occlude the tubules for a prolonged time in an acid-resistant way.

Unless otherwise indicated, all percentages, ratios, and proportions are calculated based on the weight of the total composition. All temperatures are in degrees Celsius (° C.) unless otherwise indicated. All measurements made are at 25° C., unless otherwise designated. All component or composition levels are in reference to the active level of that component or composition, and are exclusive of impurities, for example, residual solvents or by-products, which may be present in commercially available sources.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of treating a tooth surface comprising the steps:
   (a) contacting the tooth surface by contacting the tooth surface with a first composition comprising an organophosphate having the formula:

wherein R is a hydrocarbyl comprising 4 to 22 carbon atoms; X and Y are each independently an alkylene comprising 2 to 4 carbon atoms; a and b are each independently an integer selected from 0 to 20, and a+b is in the range from 0 to 20; $Z^1$ and $Z^2$ are each independently selected from hydrogen, hydrocarbyl comprising 1 to 26 carbons, and a counter ion, provided that at least one of $Z^1$ and $Z^2$ is hydrogen or a counter ion; and thereafter
   (b) occluding tubules exposed on the tooth surface by contacting the tooth surface with a second composition comprising a water-insoluble calcium phosphate, wherein the water-insoluble calcium phosphate has a calcium to phosphorus molar ratio from 1:1 to 10:1.

2. The method of claim 1, wherein contacting step (b) is initiated within 15 minutes after the conclusion of contacting step (a).

3. The method of claim 2, wherein R is an alkyl comprising 8 to 16 carbon atoms; a+b is from 1 to 10; and $Z^1$ and $Z^2$ are each independently selected from the group consisting of hydrogen and an alkali metal counter ion.

4. The method of claim 3, wherein at least one of $Z^1$ and $Z^2$ is an alkali metal counter ion selected from the group consisting of sodium ion and potassium ion; and
wherein the first composition comprises 0.01% to 10%, by weight, of the organophosphate.

5. The method of claim 4, wherein the organophosphate is selected from the group consisting of sodium laureth-1 phosphate, sodium laureth-2 phosphate, sodium laureth-3 phosphate, sodium laureth-4 phosphate, potassium laureth-1 phosphate, sodium laureth-9 phosphate, sodium myreth-2 phosphate, sodium pareth-1 phosphate, and mixtures thereof.

6. The method of claim 5, wherein the first composition comprises 0.05% to 5%, by weight, of sodium laureth-1 phosphate.

7. The method of claim 2, wherein the second composition further comprises a water-soluble fluoride source.

8. The method of claim 7, wherein the water-soluble fluoride source is selected from the group consisting of sodium fluoride, stannous fluoride, sodium monofluorophosphate, amine fluoride, and mixtures thereof; and wherein the first composition comprises 0.01% to 10%, by weight, of sodium laureth-1 phosphate.

9. The method of claim 2, wherein the water-insoluble calcium phosphate is selected from the group consisting of apatite, calcium halide phosphate, dicalcium phosphate, tricalcium phosphate, octacalcium phosphate, and mixtures thereof.

10. The method of claim 9, wherein the second composition comprises 0.1% to 20%, by weight, of apatite.

11. The method of claim 10, wherein the second composition comprises 1% to 5%, by weight, of hydroxyapatite.

12. The method of claim 2, wherein the first composition is a toothpaste composition and the second composition is a mouth rinse.

13. The method of claim 2, wherein the first composition and the second composition are each a mouth rinse.

14. The method of claim 2, wherein the second composition is a mouth rinse, with a viscosity from 2000 cps to 8000 cps.

15. The method of claim 2, wherein the first composition has a pH from 6 to 8.

16. The method of claim 2, wherein the second composition has a pH from 7 to 10.

17. The method of claim 2, wherein contacting steps (a) and (b) each independently has a contacting duration from 5 seconds to 5 minutes; and contacting step (b) is initiated immediately after the conclusion of contacting step (a).

18. The method of claim 17, wherein the first composition is a mouth rinse comprising 0.05% to 5%, by weight, of sodium laureth-1 phosphate and 0.01% to 1%, by weight, of a sodium fluoride, and the second composition is a mouth rinse comprising 1% to 5%, by weight, of hydroxyapatite; and wherein the second composition has a pH from 7 to 9 and a viscosity from 2000 cps to 8000 cps.

* * * * *